United States Patent [19]

Hope

[11] Patent Number: Plant 5,612

[45] Date of Patent: Dec. 24, 1985

[54] IMPATIENS PLANT NAMED VISTA IMPATIENS NO. 43

[75] Inventor: Claude Hope, Cartago, Costa Rica

[73] Assignee: Pan American Plant Company, Parrish, Fla.

[21] Appl. No.: 566,503

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of impatiens plant named Vista Impatiens No. 43, characterized by its large and red-purple flowers, with each flower having a white eye, dark green foliage, floriferous habit, dense compact habit, and its good self-branching and moderate rate of growth, making it ideal for hanging baskets, bedding plants and pot culture.

1 Drawing Figure

The present invention relates to a new and distinctive cultivar of impatiens plant, botanically known as *Impatiens,* and known by the varietal name Vista Impatiens No. 43.

The new cultivar was developed by me from a planned program of hybridization which had for its purpose the obtaining of a series of plants having a wide range of colors and very large flowers derived from the New Guinea complex of species collected by the Longwood Garden Expedition of 1970. The new cultivar was selected in 1981, and designated seedling No. 3307-88-3. The parents were seedling No. 3229-8 (from Impatiens Schlecterii P.I. 354260) x 1588-664-7-1 (from Impatiens Schlecterii Variety Mount Kum P.I. 354253).

Asexual reproduction of the new cultivar by terminal or stem cuttings taken at Cartago, Costa Rica has shown that the unique features of the new cultivar are stabilized and reproduced true to type in successive propagations.

The following characteristics distinguish the new impatiens from both its parent varieties and other cultivated impatiens of this type known and used in the floriculture industry:

1. Vista Impatiens No. 43 was selected primarily for its vivid red-purple color flower and white center eye.
2. Plant flowers profusely under optimum temperatures (80° F. days and 60° F. nights).
3. Plant habit is compact (38–45 cm. tall) and spreading (45–60 cm. diameter), making it ideal for hanging baskets, bedding plants and pot culture.
4. Rate of growth is moderate, producing in 6–8 weeks a saleable plant 18–25 cm. tall and 20–25 cm. in diameter (in 5½" pot) when grown outside under full sun in fall, winter and spring, and under light shade in the summer months in Florida.
5. Foliage is dark green in color and dense, providing a pleasing contrast to the flowers. The foliage maintains good color throughout the season.
6. Exhibits good self-branching habits.
7. Flowers are large (54–60 mm. in diameter).

The accompanying colored photograph illustrates the overall appearance of this cultivar, showing the colors as true as it is reasonably possible to obtain in a colored reproduction of this type.

The following is a detailed description of my new impatiens cultivar based on plants produced under commercial practice in Cortez and Parrish, Fla. The plants were produced outdoors in full sun during the fall, winter and spring months and under light shade during the summer months. Color references are made to The Royal Horticultural Society Colour Chart except where general terms of ordinary dictionary significance are used.

Parentage: Seedling No. 3229-8 (from Impatiens Schlecterii P.I. 354260) x 1588-664-7-1 (from Impatiens Schlecterii Variety Mount Kum P.I. 354253).

Propagation:

A. *Type cutting.*—Tip cuttings with 5 cm. stems.

B. *Time to initiate roots.*—10–14 days at 27° C. summer; 12–16 days at 18° C. winter.

C. *Rooting habit.*—Abundant and fibrous.

Plant description:

A. *Form.*—Relatively short and compact (38 cm.—45 cm. tall when full grown); dense foliage; low dome-shaped plant.

B. *Habit of growth.*—Rate of growth moderate for this type of plant. Vegetative shoots are formed at the lower nodes and flowers at the higher nodes.

C. *Foliage description.*—Lower leaves opposite, higher leaves in whorls of 5–7. Leaves are simple. (1) Size: Average full grown leaf is 100 mm. long×46 mm. wide. Full grown leaves have petioles 25 mm. long. Young leaves have very short to no petioles. (2) Shape: Elliptic, apex acuminate, base attenuate. (3) Texture: Smooth surface, glabrous. (4) Margin: Serrulate. (5) Color: Young foliage, top side close to green 143A, under side green 138B; mature foliage, top side green 137A, under side green 138B. (6) Venation: Pinnate, main vein yellow green 145C.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperature in Florida.

C. *Flower bud description.*—Conical, covered with 3 sepals; upper two sepals are 10 mm. long×6 mm. wide, apex acuminate; lower sepal is 13 mm. long×10 mm. wide, apex acuminate. Upper sepals are green and the lower sepal is colorless infused slightly with green at the apex. Apex itself is green. Hollow spur connected to the lower sepal is 52 mm. long when full grown and is cream slightly infused with pink.

D. *Flowers borne.*—On peduncles 45 mm. long.

E. *Quantity of flowers.*—One flower per leaf, occurring progressively around the whorl of leaves.

F. *Petals.*—(1) Shape: Top petal heart-shaped with a wide rounded base. Other petals are heart-shaped with pointed bases. (2) Color, top side is close to red-purple 74A when opening, with a large white eye infused with a middle stripe of pink. The main petal color fades to red-purple 74B. The under side is close to and between 74B and C. (3) Number of petals: Five. (4) Size of flowers: Top petal is 20 mm. long×36 mm. wide; 2 middle petals are 26 mm. long×19 mm. wide; 2 lower petals are 30 mm. long×21 mm. wide. Total flower diameter is 56 mm.

G. *Reproductive organs.*—(1) Stamens: Five, with the lower stamen being shorter than the others.

Stamens united in an asymmetrical tube surrounding and covering the ovary. (a) Anthers. Hooded, colorless infused with pink. (b) Pollen color: Cream. (2) Pistils: (a) Stigma: Five pointed star, colorless. (b) Styles: Cream to light green in color. (c) Ovaries: 5, celled, size 4–5 mm. green in color.

Disease resistance: No general plant diseases noted. Insect problems can include the two spotted spider mite which can cause foliar injury and thrips which can cause stunting and injury to the growing tip.

I claim:

1. A new and distinct cultivar of impatiens plant named Vista Impatiens No. 43, as described and illustrated, and characterized by its large red-purple flowers, with each flower having a white eye, dark green foliage, floriferous habit, dense compact habit, and its good self-branching and moderate rate of growth, making it ideal for hanging baskets, bedding plants and pot culture.

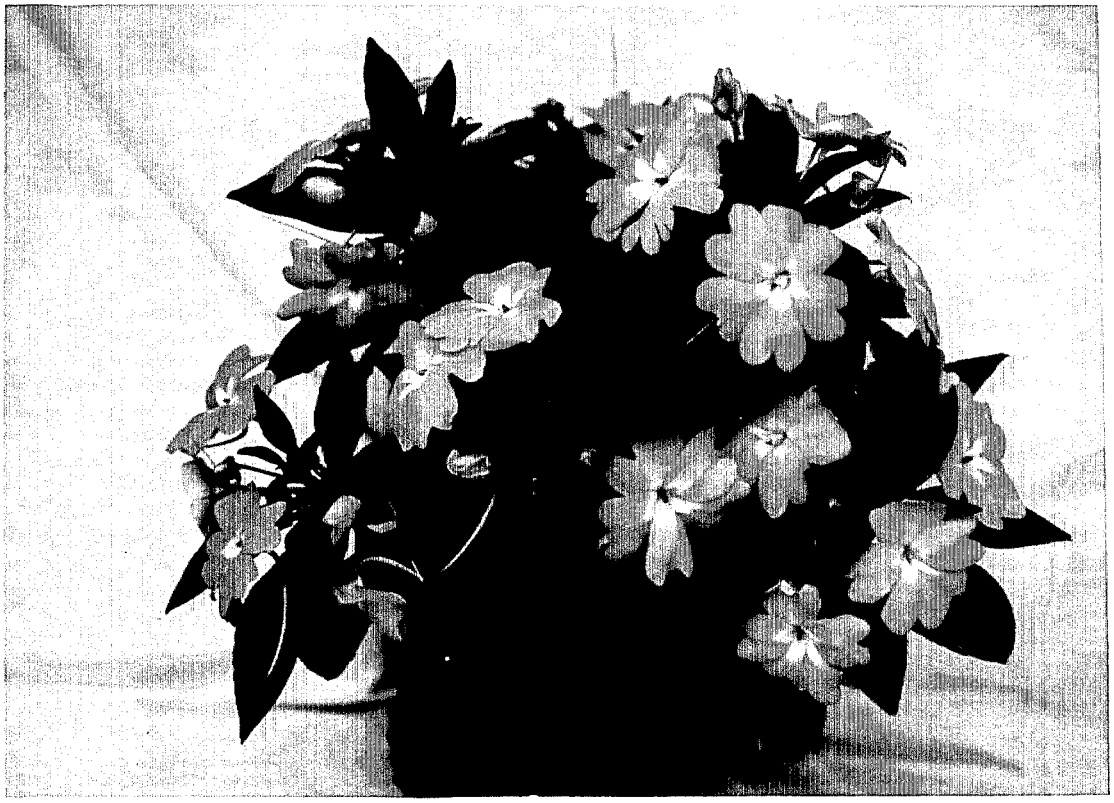

* * * * *